United States Patent
Hill et al.

(10) Patent No.: US 9,211,354 B2
(45) Date of Patent: Dec. 15, 2015

(54) BULKHEAD ASSEMBLY FOR VHP UNIT WITH REMOVABLE DIFFUSER

(71) Applicant: American Sterilizer Company, Mentor, OH (US)

(72) Inventors: Aaron L. Hill, Madison, OH (US); Ryan A. Bruskevith, Mentor, OH (US); Leslie M. Logue, Edinboro, PA (US); William D. Warren, Pepper Pike, OH (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 372 days.

(21) Appl. No.: 13/627,122

(22) Filed: Sep. 26, 2012

(65) Prior Publication Data

US 2013/0078153 A1    Mar. 28, 2013

Related U.S. Application Data

(60) Provisional application No. 61/540,052, filed on Sep. 28, 2011.

(51) Int. Cl.
| | |
|---|---|
| *A61L 2/20* | (2006.01) |
| *A61L 2/22* | (2006.01) |
| *A61L 2/18* | (2006.01) |

(52) U.S. Cl.
CPC .. *A61L 2/22* (2013.01); *A61L 2/186* (2013.01); *A61L 2202/15* (2013.01)

(58) Field of Classification Search
CPC ........................................................ A61L 2/20
USPC ........................................ 422/111, 292, 300
See application file for complete search history.

(56) References Cited

U.S. PATENT DOCUMENTS

| 2,690,380 A | 9/1954 | Taylor ............................. 23/204 |
| 2,795,015 A | 6/1957 | Foley .............................. 52/291 |

(Continued)

FOREIGN PATENT DOCUMENTS

| DE | 42 37 061 | 1/1994 | ............. E05C 19/00 |
| GB | 2 196 048 | 4/1988 | ............. E04G 21/18 |

(Continued)

OTHER PUBLICATIONS

Supplemental European Search Report dated May 15, 2015 from Application No. 12834502.2.

(Continued)

*Primary Examiner* — Sean E Conley
(74) *Attorney, Agent, or Firm* — Kusner & Jaffe; Michael A. Centanni

(57) ABSTRACT

A system for decontaminating an enclosure that defines a region. The system includes a decontamination unit for generating a vaporized sterilant. The decontamination unit includes a housing that defines a chamber therein. An inlet and an outlet of the housing fluidly communicate with the chamber. A bulkhead assembly connects the decontamination unit to the enclosure. The bulkhead assembly includes a barrier assembly for sealing an opening of the enclosure. The membrane traverses the opening of the enclosure. A first port and a second port allow the carrier gas to flow through the membrane. A frame assembly seals the barrier assembly into the opening of the enclosure. An outlet conduit defines a flow path for conveying the carrier gas from the decontamination unit to the region of the enclosure. A return conduit defines a flow path for conveying the carrier gas from the enclosure to the decontamination unit.

22 Claims, 8 Drawing Sheets

(56) References Cited

U.S. PATENT DOCUMENTS

| | | | |
|---|---|---|---|
| 4,133,367 A | 1/1979 | Abell | 160/368.1 |
| 4,445,563 A * | 5/1984 | Meyeroff | E06B 3/28 |
| | | | 160/368.1 |
| 4,537,749 A | 8/1985 | Hick | 422/304 |
| 4,742,667 A | 5/1988 | Müller et al. | 53/167 |
| 5,007,232 A | 4/1991 | Caudill | 53/426 |
| 5,152,968 A | 10/1992 | Foti et al. | 422/304 |
| 5,737,885 A * | 4/1998 | Stoyke | 52/202 |
| 5,835,677 A | 11/1998 | Li et al. | 392/401 |
| 5,906,794 A | 5/1999 | Childers | 422/28 |
| 5,932,256 A | 8/1999 | Mandish | 425/405.1 |
| 6,406,666 B1 | 6/2002 | Cicha et al. | 422/28 |
| 6,746,652 B2 | 6/2004 | Khorzad et al. | 422/305 |
| 7,156,957 B1 | 1/2007 | Parrish et al. | 204/157.3 |
| 7,186,374 B2 | 3/2007 | Zelina et al. | 422/28 |
| 7,252,800 B2 | 8/2007 | Jacobs et al. | 422/33 |
| 2003/0133834 A1 | 7/2003 | Karle | 422/33 |
| 2004/0005259 A1 | 1/2004 | Sacca | 422/295 |
| 2004/0022673 A1 | 2/2004 | Protic | 422/28 |
| 2004/0146437 A1 | 7/2004 | Arts et al. | 422/186.07 |
| 2006/0041994 A1 | 3/2006 | Germain et al. | 2/457 |
| 2007/0181271 A1 | 8/2007 | Earnest | 160/368.1 |
| 2007/0253859 A1 | 11/2007 | Hill | 422/3 |
| 2007/0274858 A1 | 11/2007 | Childers et al. | 422/28 |
| 2008/0247922 A1 | 10/2008 | Adams et al. | 422/292 |
| 2008/0292498 A1 | 11/2008 | Resch et al. | 422/29 |

FOREIGN PATENT DOCUMENTS

| | | | |
|---|---|---|---|
| GB | 2196048 A | 4/1988 | E04G 21/18 |
| JP | S55-113082 | 8/1980 | A01M 13/00 |
| JP | H02-274253 A | 11/1990 | A61J 1/05 |
| JP | H05-37245 | 5/1993 | A61L 2/20 |
| JP | H11-19194 A | 1/1999 | A61L 2/20 |
| JP | 2000-513247 | 10/2000 | A61L 2/20 |
| JP | 2001-276189 A | 10/2001 | A61L 2/20 |
| JP | 2005-532891 A | 11/2005 | A61L 2/20 |
| JP | 2008-526466 | 7/2008 | A61L 2/20 |
| JP | 2008-544830 A | 12/2008 | A61L 2/20 |
| WO | WO 97/47331 | 12/1997 | A61L 2/20 |
| WO | WO 2007/102798 | 1/2007 | A61L 2/20 |
| WO | WO 2007/102798 | 9/2007 | A61L 2/18 |
| WO | WO 2007/109401 | 9/2007 | A61L 2/22 |
| WO | WO 2008/145990 | 12/2008 | A61L 2/20 |
| WO | WO 2011/047127 | 4/2011 | A61L 2/22 |

OTHER PUBLICATIONS

Office Action issued in connection with Japanese Patent Application No. 2014-533703 (English-language translation included) dated Apr. 14, 2015.

European Search Report dated May 5, 2015 from Application No. 12834502.2.

* cited by examiner

BULKHEAD ASSEMBLY FOR VHP UNIT WITH REMOVABLE DIFFUSER

RELATED APPLICATIONS

This application claims the benefit of U.S. Provisional Application No. 61/540,052, filed Sep. 28, 2011, which is fully incorporated herein by reference.

FIELD OF THE INVENTION

The present invention relates to an apparatus for decontaminating a region and articles disposed therein using a vaporous chemical agent.

BACKGROUND OF THE INVENTION

A region, defined by an enclosure, (e.g., hotel rooms, offices, laboratories, buildings, cruise ships, airport terminals, and the like) may be decontaminated by exposing the region (and any articles therein) to a vaporous chemical agent, such as vaporized hydrogen peroxide (VHP). Vaporized hydrogen peroxide may be generated by vaporizing a metered quantity of an aqueous solution of hydrogen peroxide. The vaporized hydrogen peroxide is carried into the region by a carrier gas (e.g., air). As used herein the term "decontamination" refers to the inactivation of bio-contamination, and includes, but is not limited to, sterilization and disinfection.

Conventionally, a VHP unit is used to generate the VHP. The VHP unit typically is placed inside the room and the room is sealed to prevent the VHP from escaping to the surrounding environment. In some cases, the end user does not wish to place the VHP unit in the room due to the increased risk of contaminating the VHP unit. Moreover, the end user may determine that it is unsafe to enter the room until the room has been properly decontaminated.

The present invention provides an apparatus for attaching a VHP unit to a region wherein the VHP unit is disposed outside of the room.

SUMMARY OF THE INVENTION

In accordance with a preferred embodiment of the present invention, there is provided a system for decontaminating an enclosure that defines a region. The system includes a decontamination unit for generating a vaporized sterilant. The decontamination unit includes a housing that defines a chamber therein. An inlet and an outlet of the housing fluidly communicate with the chamber. A blower conveys a carrier gas from the inlet, through the chamber and to the outlet of the housing. A generator introduces a vaporized sterilant into the carrier gas conveyed through the housing. A bulkhead assembly connects the decontamination unit to the enclosure. The bulkhead assembly includes a barrier assembly for sealing an opening of the enclosure. The barrier assembly includes a membrane resistant to the vaporized sterilant. The membrane traverses the opening of the enclosure. A first port and a second port allow the carrier gas to flow through the membrane. A frame assembly seals the barrier assembly into the opening of the enclosure. An outlet conduit is connected at one end to the outlet of the decontamination unit and at another end to the first port of the barrier assembly. The outlet conduit defines a flow path for conveying the carrier gas from the decontamination unit to the region of the enclosure. A return conduit is connected at one end to the inlet of the decontamination unit and at another end to the second port of the barrier assembly. The return conduit defines a flow path for conveying the carrier gas from the enclosure to the decontamination unit.

According to another embodiment of the present invention there is provided an apparatus for connecting a decontamination unit to an enclosure. The apparatus includes an outlet conduit that defines a flow path for conveying a carrier gas from the decontamination unit to the enclosure. A return conduit defines a flow path for conveying the carrier gas from the enclosure to the decontamination unit. A barrier assembly seals an opening of the enclosure. The barrier assembly includes a membrane that traverses the opening of the enclosure. An inlet port and an outlet port allow the carrier gas to flow through the membrane. A frame assembly secures the barrier assembly into the opening of the enclosure.

An advantage of the present invention is a decontamination unit for decontaminating a region.

Yet another advantage of the present invention is the provision of a decontaminating unit as described above wherein a vapor generator of the decontaminating unit is disposed outside of the region.

Another advantage of the present invention is a bulkhead assembly for allowing the decontaminating unit to be disposed outside of the region.

Still another advantage of the present invention is the provision of a bulkhead assembly as described above that includes ports for easily and quickly connecting the decontamination unit to the region.

Yet another advantage of the present invention is the provision of a bulkhead assembly as described above that provides an adjustable frame assembly for allowing the bulkhead assembly to be easily placed in openings of various sizes.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
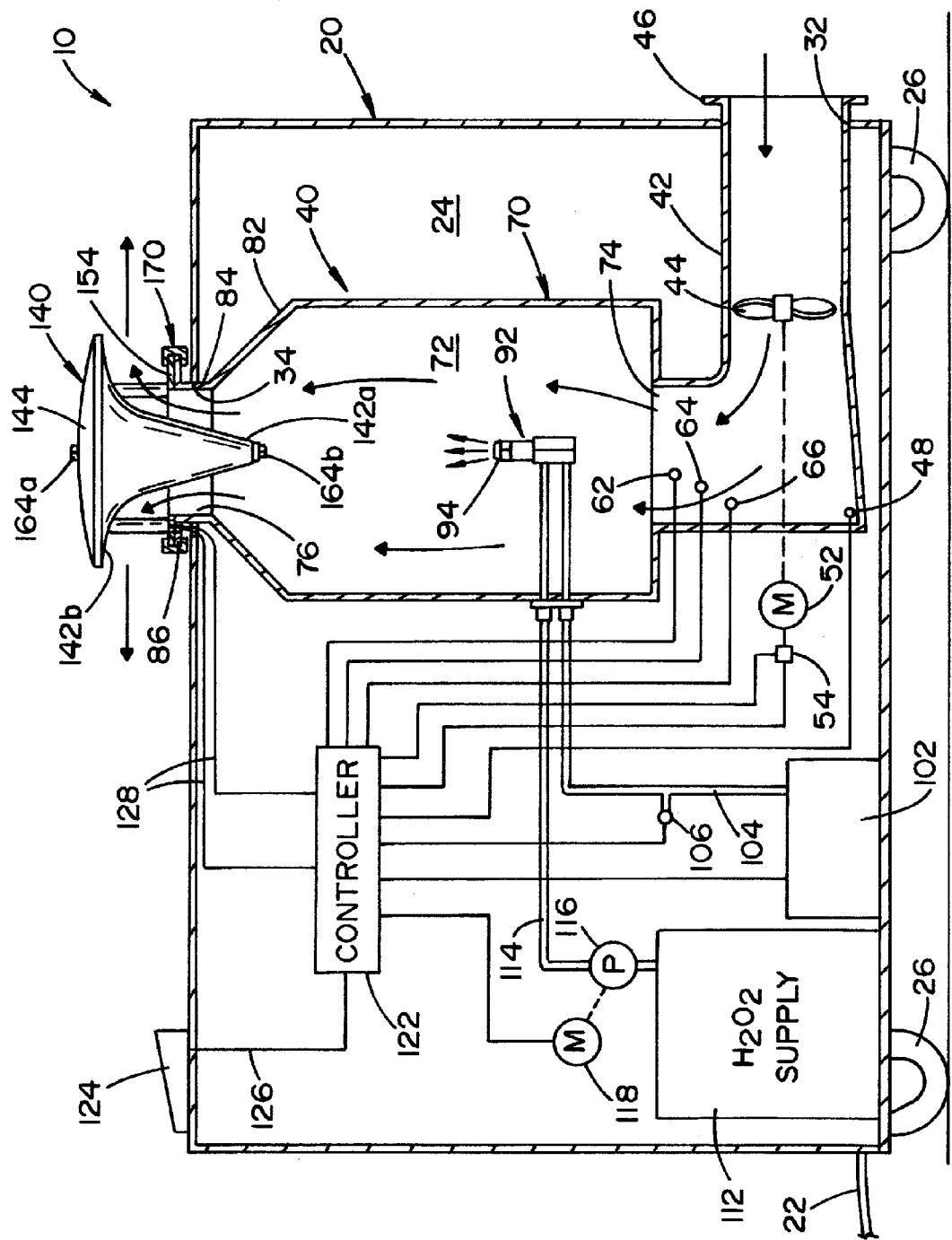
FIG. 1 is a schematic view of a decontamination unit for decontaminating a region defined by an enclosure.
Figure 3:
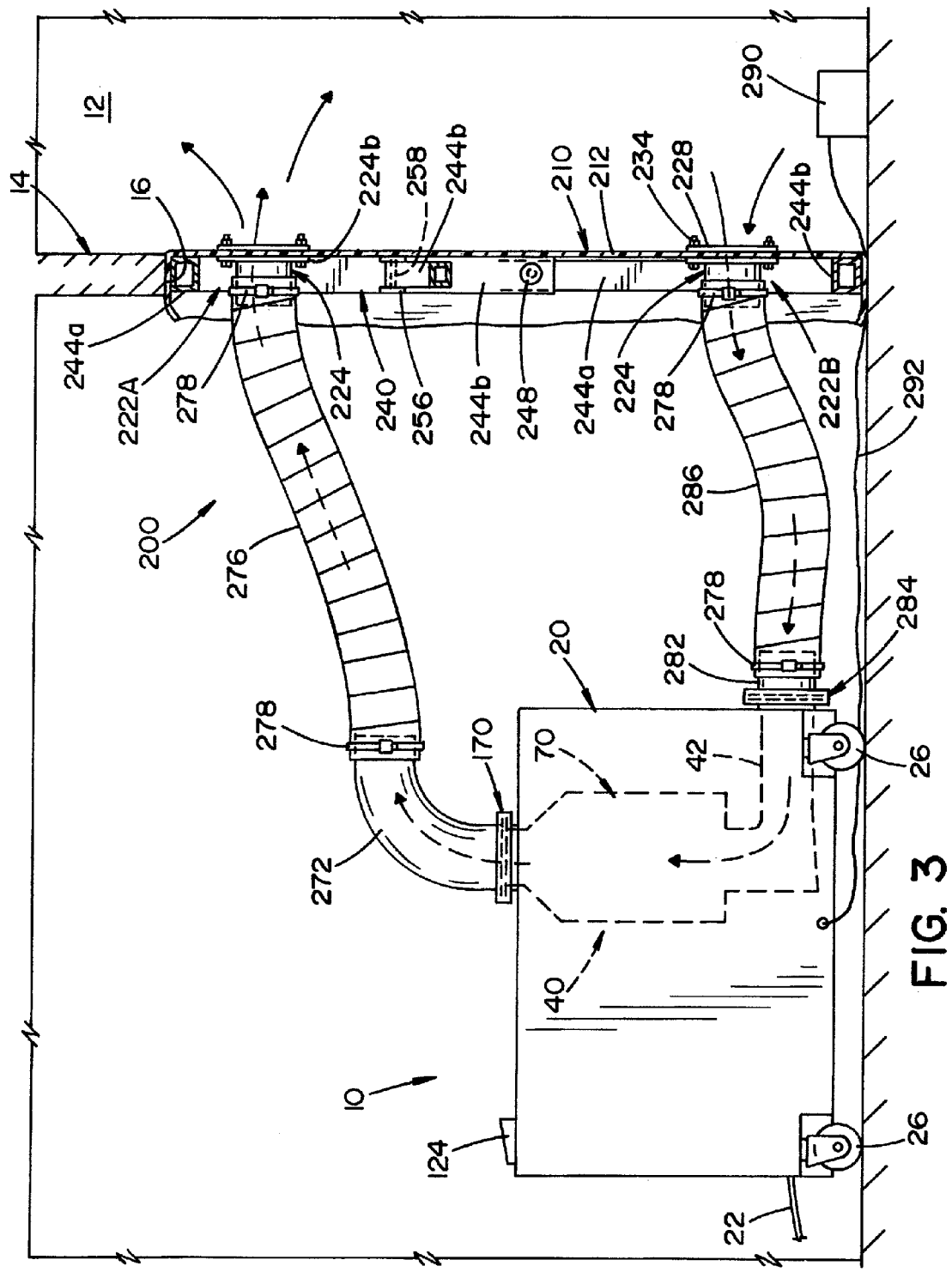
FIG. 3 is a partial cross-sectional view of a bulkhead assembly for connecting a decontamination unit to a region, according to the present invention.

Referring now to the drawings wherein the showings are for the purpose of illustrating an embodiment of the invention only, and not for the purpose of limiting same, FIG. 1 shows a schematic view of a decontamination unit 10 for decontaminating a region 12 defined by an enclosure 14. Region 12 and enclosure 14 are best seen in FIG. 3.

The present invention will be described hereinafter with reference to using decontamination unit 10 and vaporized hydrogen peroxide to decontaminate a region. However, it is appreciated that region 12 may be decontaminated using other types of chemical agents.

FIGS. 1-4 show decontamination unit 10, as described in detail in U.S. patent application Ser. No. 13/242,427, entitled "Hydrogen Peroxide Vaporizer with Heated Diffuser," hereby incorporated herein by reference. The present invention will be described hereinafter with reference to using unit 10 of the '427 application to decontaminate region 12. However, it is appreciated that other embodiments of a decontamination unit may be used to decontaminate region 12.

Unit 10 is generally comprised of an outer housing member 20, an inner flow assembly 40, an air compressor 102, a reservoir 112, a controller 122, and a diffuser 140. A cable 22 is provided for connecting the components of unit 10 that require power to a power source (not shown). Inner flow assembly 40, air compressor 102, reservoir 112 and controller 122 are disposed in an inner cavity 24 defined by outer housing member 20.

Wheels 26 are attached to outer housing member 20 to allow for convenient movement of unit 10. Outer housing member 20 includes a first opening 32 and a second opening 34. First opening 32 is formed in a side wall of outer housing member 20. Second opening 34 is formed in a top wall of outer housing member 20.

Inner flow assembly 40 is generally comprised of a conduit 42, a blower 44, and an inner housing 70. Conduit 42 includes an inlet end that extends through first opening 32 of outer housing member 20 and an outlet end that connects to inner housing 70. A flange 46 extends outwardly from the inlet end of conduit 42. A bottom wall of conduit 42 is sloped downwardly toward a corner of conduit 42 to define a low region or sump of conduit 42.

A proximity sensor 48 is disposed in the sump of conduit 42. Sensor 48 provides a signal to controller 122 indicative of the presence or absence of aqueous hydrogen peroxide in the sump of conduit 42.

Blower 44 is disposed in conduit 42 for conveying air from the inlet end of conduit 42 to the outlet end of conduit 42. In one embodiment, blower 44 circulates air through conduit 42 at a rate of about 600 cubic feet per minute (CFM). Blower 44 is driven by a motor 52. A current sensor 54 is attached to power leads that extend from motor 52 to provide a signal to controller 122 indicative of the amount of current passing through motor 52.

A temperature sensor 62, a humidity sensor 64 and a vaporized hydrogen peroxide (VHP) sensor 66 are disposed in conduit 42. Temperature sensor 62 provides a signal to controller 122 indicative of the temperature of the air conveyed through conduit 42. Humidity sensor 64 provides a signal to controller 122 indicative of the concentration of water vapor (e.g., relative humidity (RH)) in the air conveyed through conduit 42. Absolute humidity may be determined from the temperature and RH sensed respectively by temperature sensor 62 and humidity sensor 64, or alternatively humidity sensor 64 can take the form of a sensor that directly measures absolute humidity. VHP sensor 66 provides a signal to controller 122 indicative of the concentration of vaporized hydrogen peroxide in the air conveyed through conduit 42. VHP sensor 66 is preferably a near infrared (IR) sensor or an electrochemical sensor. It is contemplated that one or more of temperature sensor 62, humidity sensor 64 and VHP sensor 66 may be disposed external to unit 10, as described below.

Figure 2:
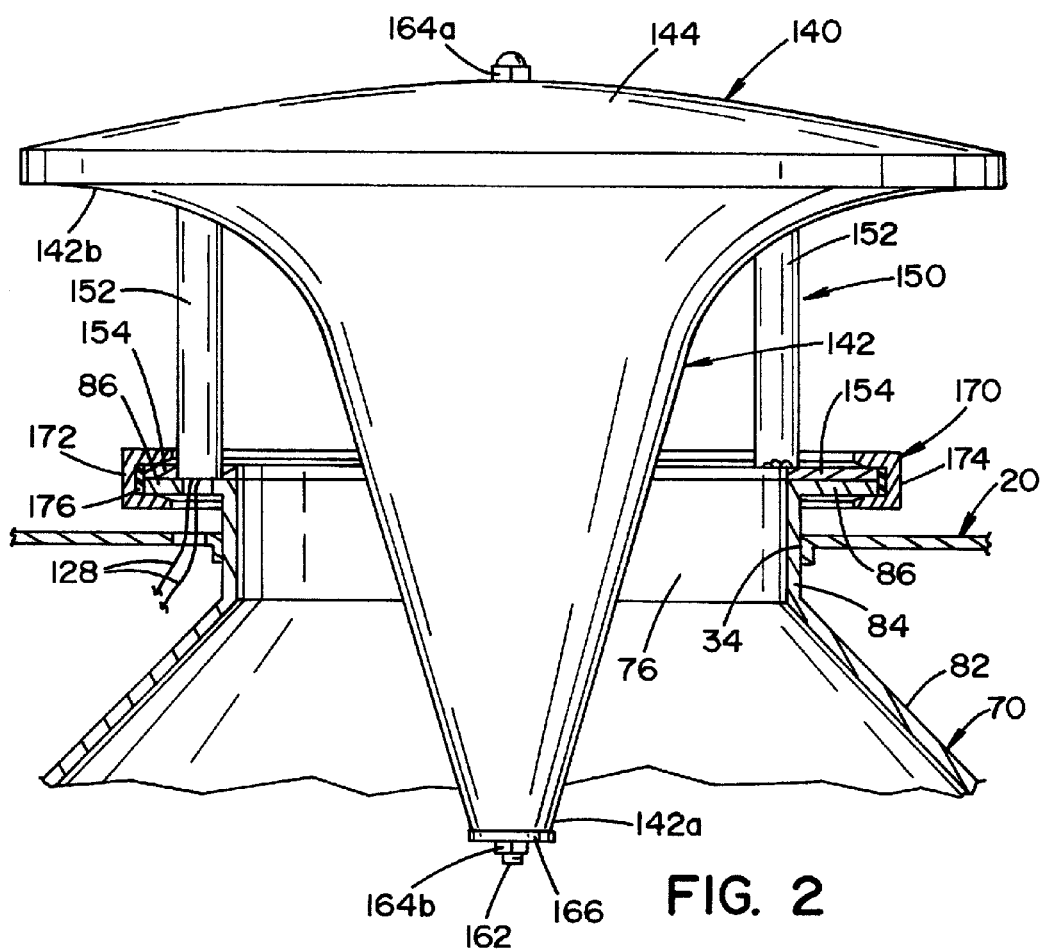
FIG. 2 is a partial cross-sectional view of the decontamination unit showing a heated diffuser attached to a top of the unit.

Inner housing 70 defines a vaporization chamber 72 therein. An inlet 74 and an outlet 76 are formed in inner housing 70 to communicate with chamber 72. Inlet 74 of inner housing 70 communicates with the outlet end of conduit 42. Outlet 76 of inner housing 70 extends through second opening 34 of outer housing member 20. As shown in FIG. 2, an upper section of inner housing 70 includes a tapered portion 82 and a collar portion 84. Collar portion 84 defines outlet 76 of inner housing 70. An outwardly extending annular flange 86 is disposed on an end of collar portion 84. Collar portion 84 of inner housing 70 extends through second opening 34 in outer housing member 20 such that flange 86 is disposed outside of outer housing member 20.

An atomizer 92 is disposed within chamber 72. Atomizer 92 includes a nozzle 94 that is oriented toward outlet 76 of inner housing 70. In the embodiment shown, atomizer 92 produces droplets that are approximately 2 microns in diameter.

Air compressor 102 is provided to supply pressurized air to atomizer 92. A line 104 connects air compressor 102 to atomizer 92. A pressure sensor 106 is disposed in line 104. Pressure sensor 106 provides a signal to controller 122 indicative of the pressure of the air in line 104.

Reservoir 112 is provided for holding a predetermined amount of an aqueous solution of hydrogen peroxide. A line 114 connects reservoir 112 to atomizer 92. A pump 116 is disposed in line 114 to convey metered amounts of the aqueous solution of hydrogen peroxide from reservoir 112 to atomizer 92. In the embodiment shown, pump 116 includes an encoder (not shown) that allows monitoring of the amount of the aqueous solution of hydrogen peroxide that is metered to atomizer 92. Pump 116 is driven by a motor 118. Motor 118 may have variable speeds such that pump 116 provides variable amounts of the aqueous solution of hydrogen peroxide from reservoir 112 to atomizer 92.

Controller 122 may include a microprocessor or microcontroller, memory device(s) and a wireless communications interface. An input/output means 124 (e.g., an LED or LCD display) is connected by a cable 126 to controller 122. Controller 122 is connected to air compressor 102 and motors 52, 118, proximity sensor 48, current sensor 54, temperature sensor 62, humidity sensor 64, VHP sensor 66 and pressure sensor 106 to control the operation of unit 10.

Diffuser 140 is mounted to unit 10. Diffuser 140 finds particular application when unit 10 is disposed inside a region to be decontaminated. With respect to the embodiment of unit 10 shown, diffuser 140 is adapted to be removed from unit 10 to allow for positioning of unit 10 outside of region 12. It can be appreciated from a further reading of the present application that the present invention is not limited to the specific embodiment of diffuser 140 shown in FIG. 2 and described below.

Referring now to FIG. 2, in general, diffuser 140 is comprised of a main body 142, a mounting assembly 150, a lid 144, a heating element (not shown) and a clamp assembly 170. Main body 142 is funnel-shaped with a first end 142a and a second end 142b. In the embodiment shown, the diameter of main body 142 increases continuously from a first diameter at first end 142a to a second diameter at second end 142b.

Mounting assembly 150 includes a plurality of spacers 152 and a mounting collar 154. A first end of each spacer 152 is attached to main body 142. A second end of each spacer 152 is attached to mounting collar 154. Collar 154 is a generally flat, ring-shaped element.

Lid 144 covers second end 142b of main body 142. Lid 144 is generally disc-shaped with a hole (not shown) extending through a central portion thereof. A rod 162, fasteners 164a, 164b and a washer 166 secure lid 144 to main body 142. A first end and a second end of rod 162 include threads fowled thereon. Fasteners 164a, 164b thread onto rod 162. Washer 166 is dimensioned to be disposed on the first end of rod 162.

The heater element (not shown) is disposed in main body 142. Cables 128 are connected at one end to controller 122 and at another end to the heating element to allow controller 122 to control the operation of the heating element.

Clamp assembly 170 secures diffuser 140 to flange 86 of inner housing 70. Clamp assembly 170 is similar to a conventional drum locking ring and allows for quick and easy attachment/detachment of diffuser 140 to/from inner housing 70. Clamp assembly 170 is generally comprised of a first ring portion 172, a second ring portion 174 and a gasket 176. Gasket 176 is dimensioned to be disposed around an outer peripheral edge of flange 86 and mounting collar 154. A first end of first ring portion 172 is hinged to a first end of second ring portion 174. A bolt 178 (best seen in FIG. 8) is provided for locking/unlocking a second end of first ring portion 172 to a second end of second ring portion 174. Both first ring portion 172 and second ring portion 174 have a C-shaped cross section that is dimensioned to receive mounting collar 154, gasket 176 and flange 86 therein. In this respect, clamp assembly 170 is provided for easily and quickly attaching/detaching diffuser 140 to/from flange 86 of inner housing 70.

As noted above, the present invention finds particular application where an end user wishes to place decontamination unit 10 outside of enclosure 14. According to the present invention, a bulkhead assembly 200 attaches to an opening 16 of enclosure 14 for fluidly connecting unit 10 to region 12.

Referring now to FIGS. 3-8, bulkhead assembly 200, according to a preferred embodiment of the present invention, is shown. Bulkhead assembly 200 includes a barrier assembly 210, a frame assembly 240, an outlet conduit 276 and a return conduit 286.

Figure 5:
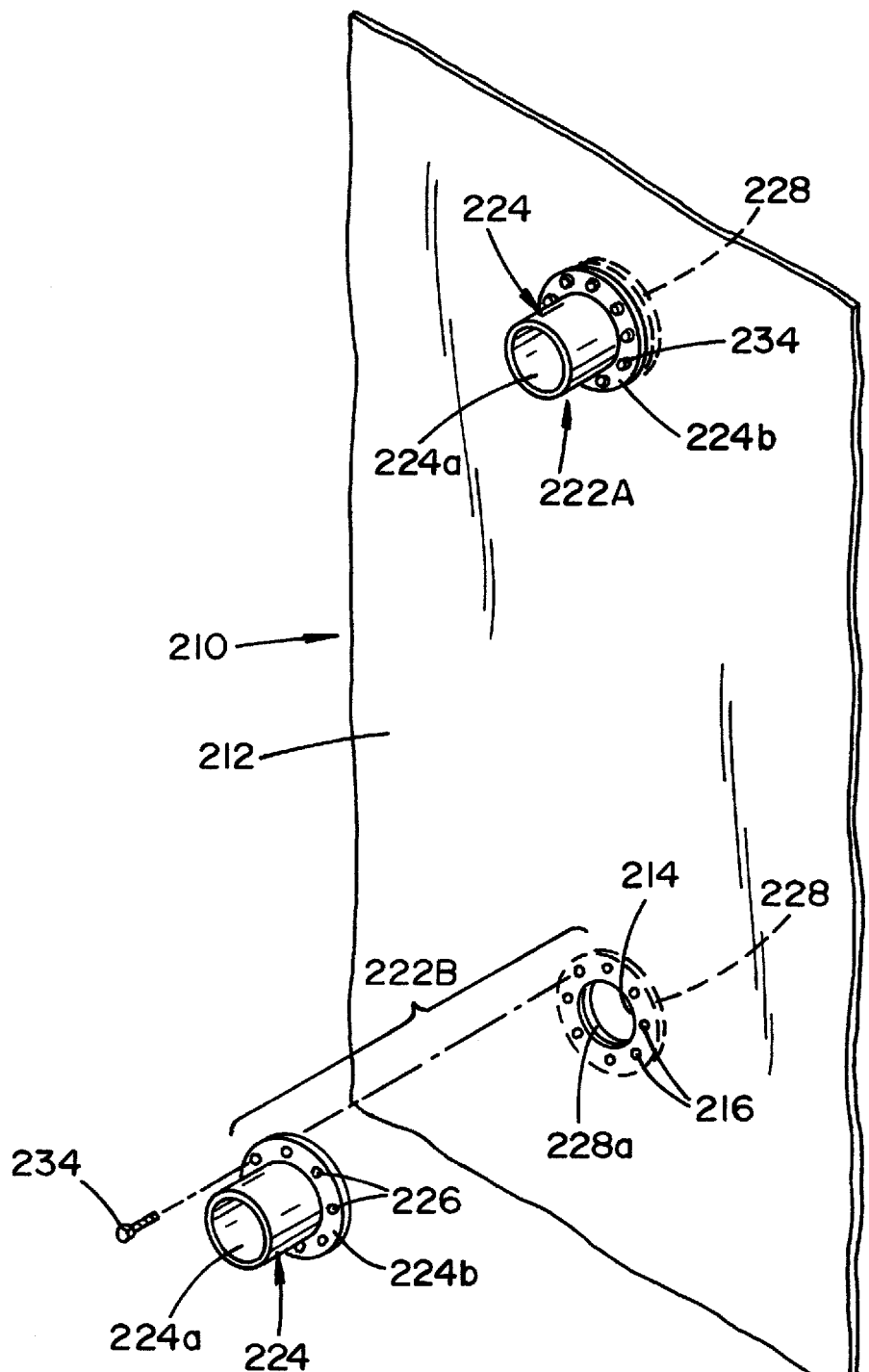
FIG. 5 is a perspective view of a barrier assembly of the bulkhead assembly shown in FIG. 4.

Barrier assembly 210, best seen in FIG. 5, includes a flexible membrane 212, a first port assembly 222A and a second port assembly 222B. Membrane 212 is made from a material that is resistant to vaporized hydrogen peroxide. A first opening (not shown) and a second opening 214 are formed in flexible membrane 212. A first plurality of spaced-apart holes (not shown) is disposed around the first opening. The holes are located an equal distance from a central axis of the first opening. A second plurality of spaced-apart holes 216 is disposed around second opening 214. Holes 216 are located an equal distance from a central axis of second opening 214.

First port assembly. 222A defines an inlet port of barrier assembly 210. Second port assembly 222B defines an outlet port of barrier assembly 210. First port assembly 222A and second port assembly 222B are essentially identical. Therefore, only second port assembly 222B will be described in detail.

Figure 7:
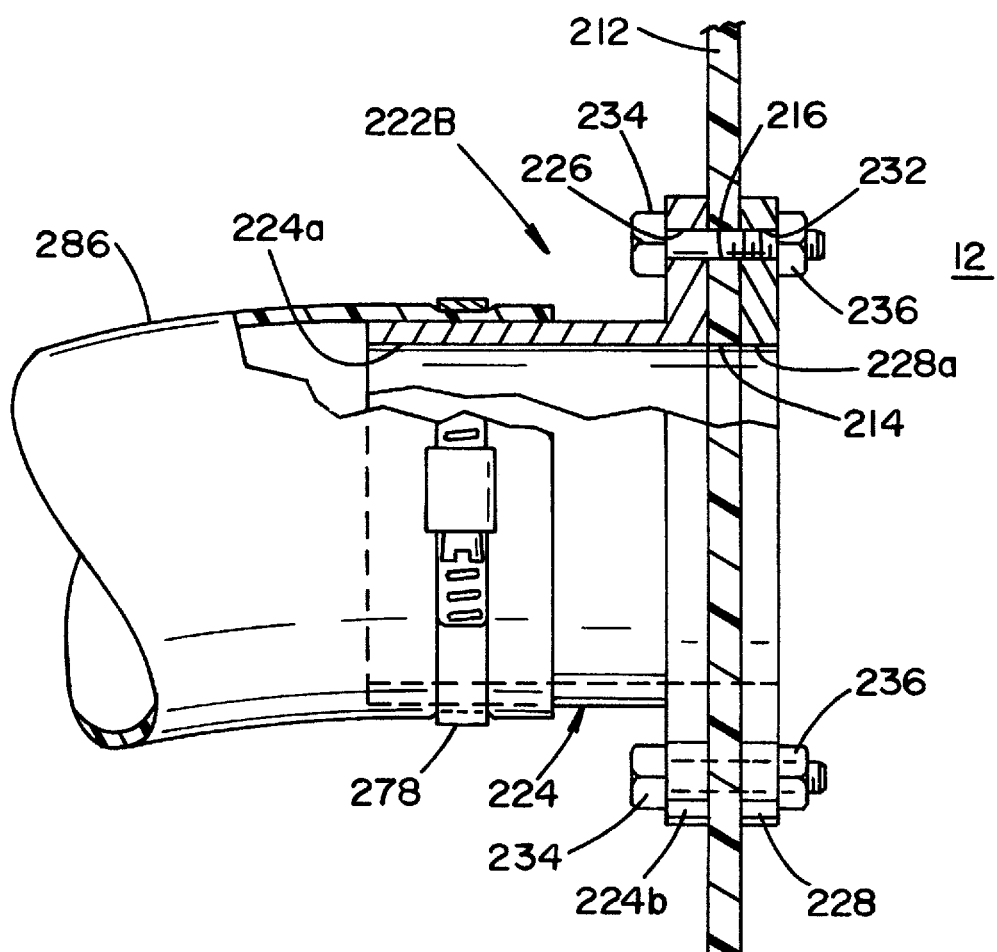
FIG. 7 is a partial cross-sectional view of a conduit connected to a port of the barrier assembly shown in FIG. 5.

Second port assembly 222B, best seen in FIG. 7, includes a first section 224 and a second section 228. First section 224 is tubular in shape and defines an opening 224a that extends from a first end to a second end thereof. An outwardly extending flange 224b is formed at the second end of first section 224. A plurality of spaced-apart holes 226 extend through flange 224b. Second section 228 of second port assembly 222B is a flat, ring-shape element that defines an opening 228a therethrough. A plurality of spaced-apart holes 232 extend through second section 228.

First section 224 is disposed on one side of membrane 212 and second section 228 is disposed on an opposite side of membrane 212. As shown in FIG. 7, first section 224 and second section 228 of second port assembly 222B are positioned and dimensioned such that opening 224a of first section 224, second opening 214 of membrane 212 and opening 228a of second section 228 are in registry with each other. In addition, plurality of spaced-apart holes 226 on flange 224b of first section 224, plurality of holes 216 around second opening 214 and plurality of holes 232 of second section 228 are dimensioned and positioned such that each hole 226 is in registry with a corresponding hole 216 and a corresponding hole 232. A bolt 234 extends through each set of holes 216, 226, 232. A nut 236 threads on to an end of each bolt 234 to clamp membrane 212 between first section 224 and second section 228.

Figure 6:
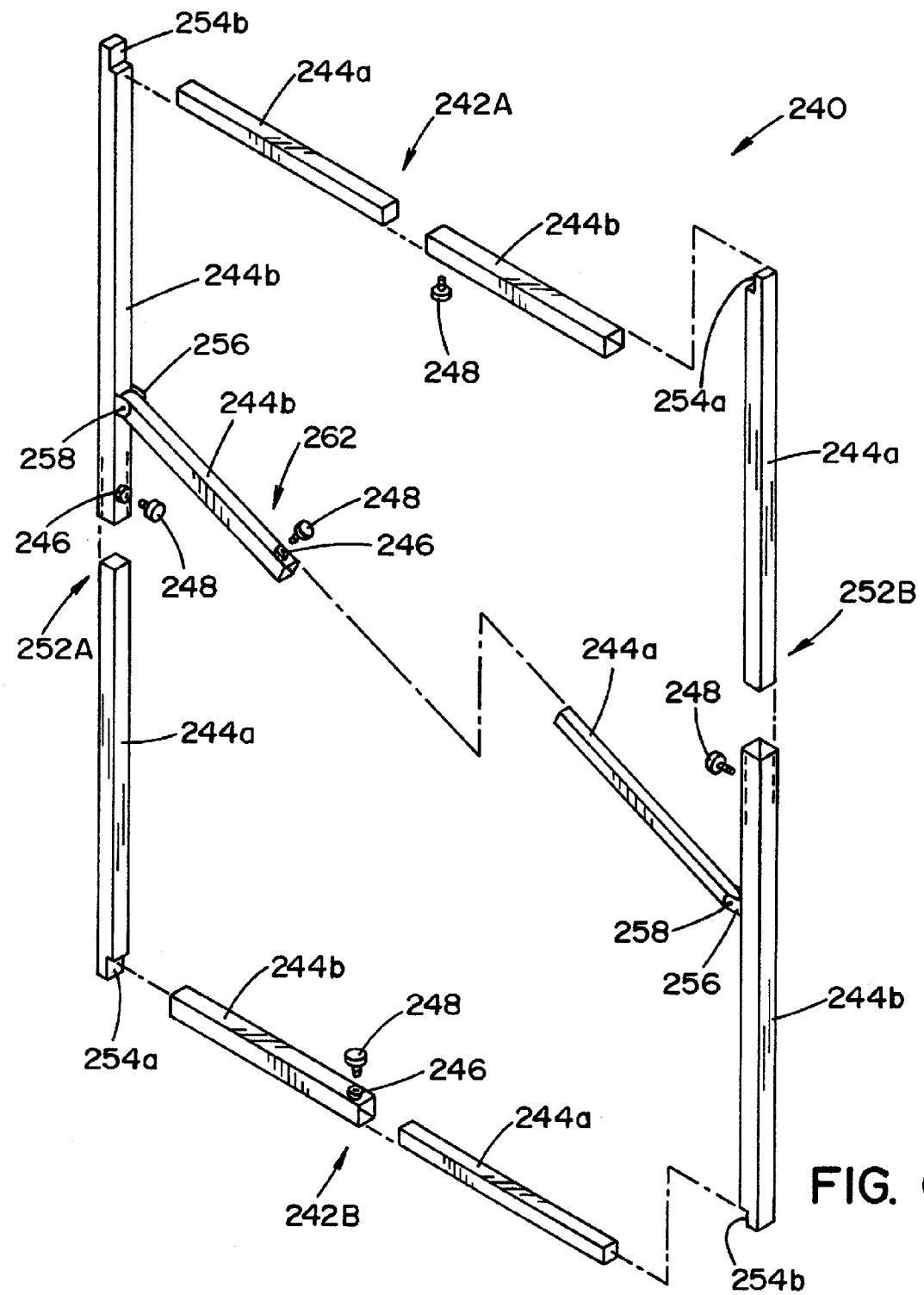
FIG. 6 is an exploded perspective view of a frame assembly of the bulkhead assembly shown in FIG. 4.

Referring to FIG. 6, frame assembly 240 is best seen. Frame assembly 240 secures barrier assembly 210 within opening 16 of enclosure 14. Frame assembly 240 generally includes five (5) telescoping assemblies for allowing the size of frame assembly 240 to be changed based on the size of opening 16 of enclosure 14. Frame assembly 240 includes an upper assembly 242A, a lower assembly 242B, a first side assembly 252A, a second side assembly 252B and a cross-brace assembly 262.

Upper and lower assemblies 242A, 242B are essentially identical and only lower assembly 242B will be described in detail. Lower assembly 242B includes an extendable member 244a and a base member 244b. Extendable member 244a is dimensioned to be nested into base member 244b and to slidingly move within base member 244b. In the embodiment shown, extendable member 244a is a rectangular-shaped rod and base member 244b is a rectangular-shaped tube. It is contemplated that extendable member 244a and base member 244b may have other shapes, such as circular or triangular.

A hole (not shown) extends through a wall of base member 244b near one end thereof. A nut 246 is attached to the outer surface of base member 244b. In particular, nut 246 is positioned to align with the hole in base member 244b. Nut 246 may be welded to base member 244b. A thumb screw 248 is dimensioned to thread into nut 246 and extend through the hole and into an inner cavity of base member 244b.

First and second side assemblies 252A, 252B are similar to upper and lower assemblies 242A, 242B. Therefore, the parts of first and second side assemblies 252A, 252B that are similar to parts of upper and lower assemblies 242A, 242B are labeled with the same reference number. Moreover, first side assembly 252A is essentially identical to second side assembly 252B. Therefore, only first side assembly 252A will be described in detail.

First side assembly 252A includes an extendable member 244a and a base member 244b, as described above for lower assembly 242B. In addition, a notch 254a is formed in one end of extendable member 244a of first side assembly 252A. Another notch 254b is formed in one end of base member 244b of first side assembly 252A. Notches 254a, 254b are dimensioned as described in detail below.

A C-shaped bracket 256 is attached to base member 244b of first side assembly 252A near a mid-portion thereof. Each leg of bracket 256 includes a hole (not shown) for receiving a pin 258.

Cross-brace assembly 262 is connected at one end to bracket 256 of first side assembly 252A and at another end to bracket 256 of second side assembly 252B. Cross-brace assembly 262 is similar to upper and lower assemblies 242A, 242B. Therefore, the parts of cross-brace assembly 262 that are similar to parts of upper and lower assemblies 242A, 242B are labeled the same reference number.

Cross-brace assembly 262 includes an extendable member 244a and a base member 244b, as described above for lower assembly 242B. A through-hole (not shown) extends through one end of extendable member 244a of cross-brace assembly 262. Another through-hole (not shown) extends through an end of base member 244b of cross-brace assembly 262. Each of the foregoing through-holes is dimensioned to receive pin 258.

Cross-brace assembly 262 is attached to first side assembly 252A and to second side assembly 252B. In particular, the through-hole in one end of base member 244b of cross-brace assembly 262 is positioned and dimensioned to align with the holes in bracket 256 of first side assembly 252A. Pin 258 is inserted into the holes in bracket 256 and into the through-hole in the end of base member 244b to pivotally connect cross-brace assembly 262 to first side assembly 252A. Similarly, the through-hole in one end of extendable member 244a of cross-brace assembly 262 is positioned and dimensioned to align with the holes in bracket 256 of second side assembly 252B. Pin 258 is inserted into the holes in bracket 256 and into the through-hole in the end of extendable member 244a to pivotally connect cross-brace assembly 262 to second side assembly 252B.

Extendable member 244a of upper and lower assemblies 242A, 242B, first and second side assembly 252A, 252B and cross-brace assembly 262 are inserted into the corresponding base member 244b of the foregoing assemblies 242A, 242B, 252A, 252B, 262. Upper assembly 242A and lower assembly 242B are then positioned into corresponding notches 254a, 254b of first and second side assemblies 252A, 252B, as shown in FIG. 6.

Figure 8:
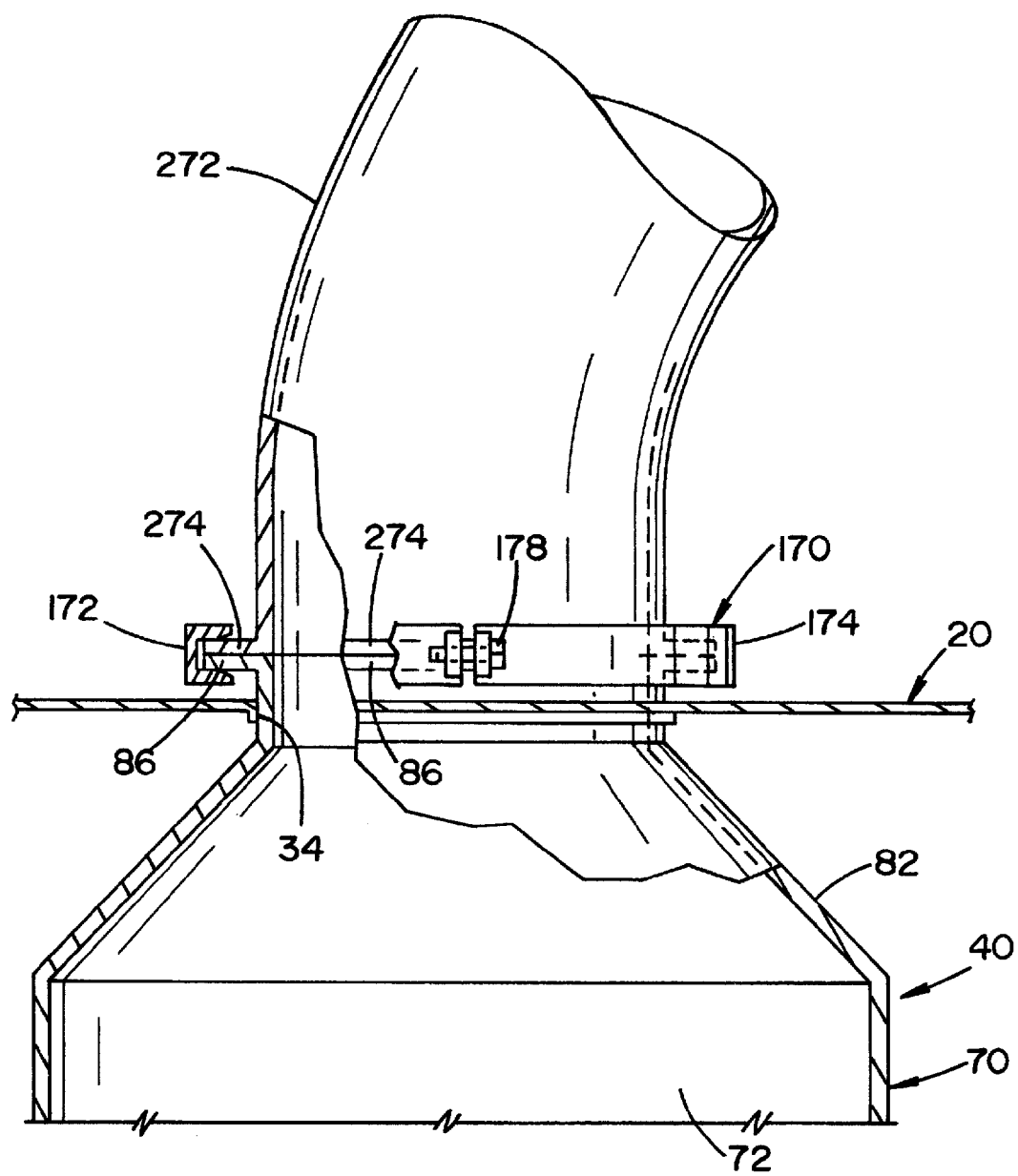
FIG. 8 is a partial cross-sectional view of an elbow of a bulkhead assembly connected to an outlet of the decontamination unit.

As noted above, the present invention finds particular application where an end user wishes to place decontamination unit 10 outside of enclosure 14. To attach unit 10 to enclosure 14, diffuser 140 is removed from inner flow assembly 40. An elbow 272 of bulkhead assembly 200 is attached to inner flow assembly 40. As best seen in FIG. 8, an outwardly extending flange 274 is disposed at one end of elbow 272. Flange 274 of elbow 272 is dimensioned to mate with flange 86 of inner flow assembly 40. Similar to diffuser 140, clamp assembly 170 secures flange 274 of elbow 272 to flange 86 of inner flow assembly 40.

Referring now to FIG. 3, outlet conduit 276 fluidly connects elbow 272 to first port assembly 222A of barrier assembly 210. Outlet conduit 276 is a flexible conduit that allows for adjustment of any slight misalignment between elbow 272 and first port assembly 222A of barrier assembly 210. Clamps 278 secure the ends of outlet conduit 276 to the end of elbow 272 and to first section 224 of first port assembly 222A. Clamp 278 is a conventional hose clamp for securing a conduit to a tubular-shaped element.

Referring again to FIG. 3, a union pipe 282 connects conduit 42 to one end of return conduit 286. A flange (not shown) of pipe 282 is dimensioned to mate with conduit 42. A clamp assembly 284 secures the flange of pipe 282 to conduit 42. Clamp assembly 284 is essentially identical to clamp assembly 170, described in detail above. Therefore clamp assembly 284 will not be described in detail.

Another end of return conduit 286 connects to second port assembly 222B of barrier assembly 210. Return conduit 286 is a flexible conduit that allows for adjustment of any slight misalignment between union pipe 282 and second port assembly 222B of barrier assembly 210. Hose clamps 278 secure one end of return conduit 286 to union pipe 282 and another end of return conduit 286 to first section 224 of second port assembly 222B. Hose clamps 278 are conventional hose clamps for securing a circular hose to a circular fitting.

According to the present invention, sensors, represented by box 290 in FIG. 3, are disposed in region 12. A cable 292 is connected at one end to the sensors and at another end to controller 122. Controller 122 receives signals from the sensors indicative of one or more measured properties, e.g., temperature, humidity, VHP concentration, in region 12. It is contemplated that temperature sensor 62, humidity sensor 64 and VHP sensor 66 may be located in box 290 instead of in unit 10 to provide signals indicative of the temperature, humidity and VHP concentration in region 12. As shown in FIG. 3, cable 292 is routed under barrier assembly 210. It is contemplated that a sealant may be used to seal any gaps formed between cable 292 and barrier assembly 210. It is also contemplated that barrier assembly 210 may include an additional port for allowing cable 292 to be fed through membrane 212.

Figure 4:
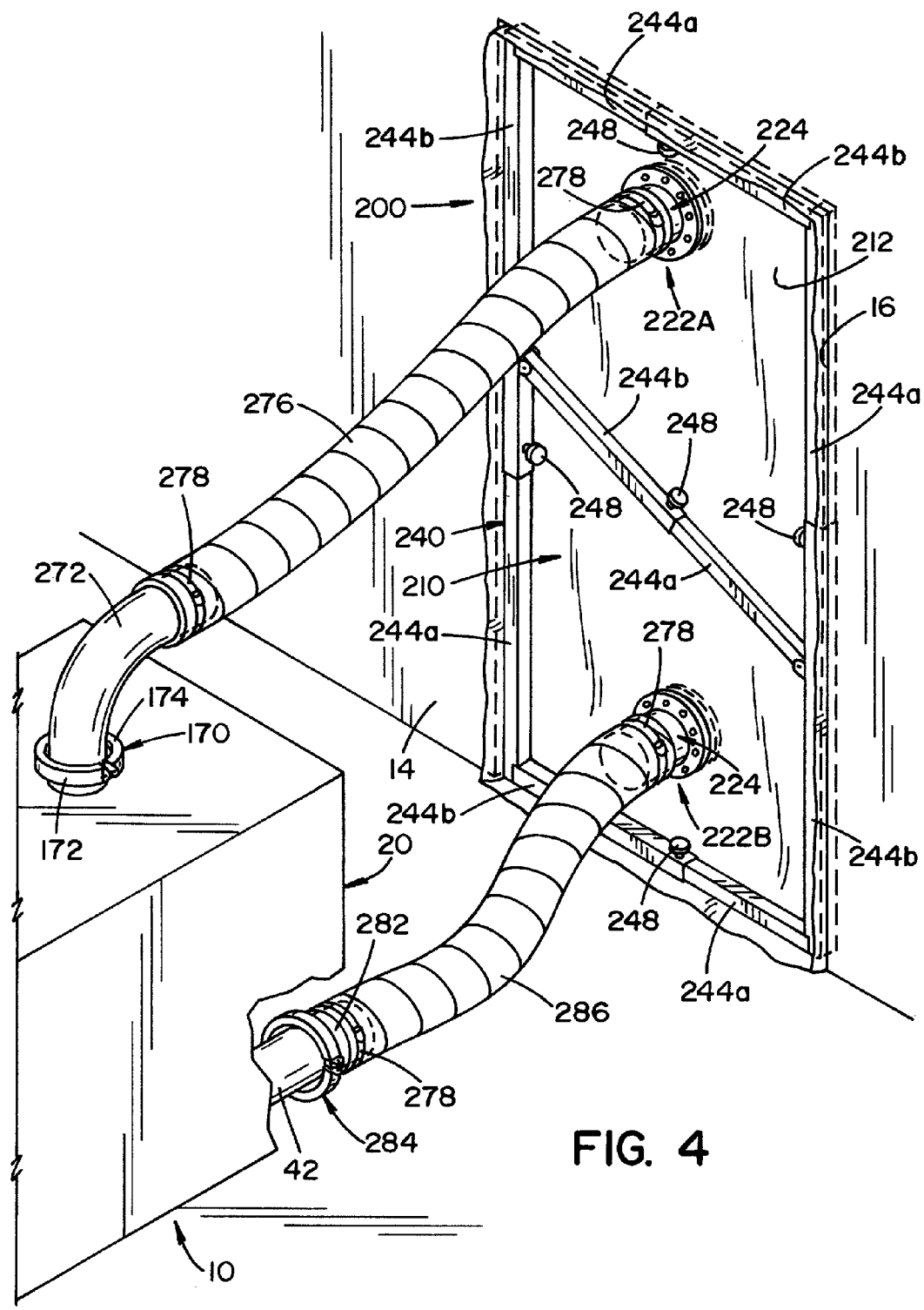
FIG. 4 is a perspective view of the bulkhead assembly and the decontamination unit shown in FIG. 3.

The operation of unit 10 will now be described in connection with the decontamination of region 12 wherein unit 10 is disposed outside of region 12. Referring now to FIGS. 3 and 4, barrier assembly 210 is placed over frame assembly 240 and frame assembly 240 is expanded to secure membrane 212 into opening 16 of enclosure 14. In particular, each extendable member 244a is extended from a corresponding base member 244b such that extendable member 244a and base member 244b extend the length of a corresponding side of opening 16 of enclosure 14. Thumb screws 248 are then tightened to lock each extendable member 244a at a desired position within a corresponding base member 244b, thereby locking frame assembly 240 into a desired configuration. In particular, frame assembly 240 is positioned within opening 16 such that membrane 212 is held tightly or taut within opening 16 of enclosure 14.

Frame assembly 240, as described above, includes at least one cross-brace assembly 262 for bracing first and second side assemblies 252A, 252B within opening 16 of enclosure 14. It is contemplated that, if opening 16 of enclosure 14 is of a sufficiently large size, frame assembly 240 may include two (2) or more cross-brace assemblies to properly brace first and second side assemblies 252A, 252B within opening 16. For example, a first cross-brace assembly 262 may be disposed at an upper portion of opening 16 and a second cross-brace assembly 262 may be disposed at a bottom portion of opening 16. As such, the foregoing cross-brace assemblies provide support to an upper portion and a lower portion of first and second side assemblies 252A, 252B.

As described in detail above, bulkhead assembly 200 is secured into opening 16 of enclosure 14. Outlet conduit 276 and return conduit 286 fluidly connect unit 10 to region 12. In particular, the present invention provides a bulkhead assembly 200 wherein frame assembly 240 includes telescoping sections for allowing bulkhead assembly 200 to be placed in a variety of openings of different sizes. The telescoping sections of frame assembly 240 allow bulkhead assembly 200 to be quickly and easily re-configured to the size of opening 16 of enclosure 14.

A decontamination cycle is initiated to decontaminate region 12 and the articles disposed therein. Controller 122 is programmed to control the operation of motors 52, 118 and air compressor 102 during a decontamination cycle. Controller 122 initiates the decontamination cycle by energizing motor 52. Motor 52 activates blower 44 thereby drawing ambient air from the region, through second port assembly 222B, through return conduit 286, and into unit 10. The ambient air is conveyed through conduit 42, through vaporization chamber 72, exits through outlet 76 of inner housing 70, passes through outlet conduit 276 and through first port assembly 222A back into region 12. Current sensor 54 provides a signal to controller 122 indicative of the amount of current passing through motor 52. Based on the foregoing signal, controller 122 determines whether motor 52 is operating within predetermined acceptable operating parameters.

Controller 122 energizes air compressor 102 to supply pressurized air to atomizer 92 and energizes motor 118 to cause pump 116 to supply the aqueous solution of hydrogen peroxide to atomizer 92. In particular, controller 122 controls the speed of motor 118 to cause pump 116 to supply the aqueous solution of hydrogen peroxide to atomizer 92 at a predetermined rate. Pressure sensor 106 provides a signal to controller 122 indicative of the pressure in line 104, Based on the foregoing signal from pressure sensor 106, controller 122 determines whether air compressor 102 is operating within predetermined acceptable operating parameters.

Atomizer 92 combines the pressurized gas from air compressor 102 and the aqueous solution of hydrogen peroxide from reservoir 112 to form a fine mist of aqueous hydrogen peroxide that is injected into vaporization chamber 72. The atomized mist of hydrogen peroxide vaporizes in the ambient air to form vaporized hydrogen peroxide. The vaporized hydrogen peroxide is entrained into the ambient air circulated through chamber 72. In this respect, the ambient air acts as a carrier gas and mixes with the vaporized hydrogen peroxide to form an air/VHP mixture.

As noted above, conduit 42 includes a lower portion or sump. In the event that a portion of the aqueous hydrogen peroxide does not vaporize in chamber 72, the aqueous hydrogen peroxide will drip downwardly in chamber 72 and collect in the sump of conduit 42. Proximity sensor 48, disposed in the sump of conduit 42, provides a signal to controller 122 if a predetermined amount of aqueous hydrogen peroxide collects in the sump of conduit 42. Controller 122 is programmed such that upon receipt of the foregoing signal from proximity sensor 48, controller 122 de-energizes motor 118 and provides an alarm to the user indicating that excess aqueous hydrogen peroxide has accumulated in conduit 42.

According to the present invention, sensors in region 12, represented by box 290 provide signals to controller 122 indicative of one or more measured properties within region 12. Based on the measured properties, controller 122 controls the operation of unit 10 to decontaminate region 12.

It is contemplated that after region 12 has been exposed to a predetermined level of hydrogen peroxide for a sufficient time to decontaminate region 12, that the end user will disconnect decontamination unit 10 from bulkhead assembly 200. It is contemplated that the end user may allow the hydrogen peroxide in region 12 to naturally degrade over time until a predetermined concentration is reached. Alternatively, the end user may connect a destroyer unit and/or an aeration unit to bulkhead assembly 200, in a manner similar to the manner described in detail above. The carrier gas is circulated through the destroyer unit and/or the aeration unit to quickly reduce the concentration of hydrogen peroxide within region 12 to a level that is safe for the end user to enter region 12. Thereafter, the end user disconnects outlet conduit 276 and return conduit 286 from the destroyer unit and/or aeration unit and from first port assembly 222A and second port assembly 222B, respectively. To remove barrier assembly 210 from opening 16, the user loosens thumb screws 248 of frame assembly 240 such that the extendable members 244_a_ of frame assembly 240 retract inside of the corresponding base members 244_b_. Barrier assembly 210 may then be removed from opening 16 of enclosure 14.

It is also contemplated that bulkhead assembly 200 may be connected to a system that includes a decontamination unit, a destroyer unit and an aeration unit integrated therein. This system may include a plurality of internal valves for selectively connecting each of the foregoing units to bulkhead assembly 200. This system does not require that an end user repeatedly connect and disconnect bulkhead assembly 200 to multiple units to decontaminate a region.

The present invention thus provides a bulkhead assembly for quickly and easily connecting a unit, e.g., a decontamination unit, a destroyer unit or an aeration unit, to an enclosure in a manner that allows an end user to position the unit outside of the region. The present invention provides a barrier assembly for fluidly isolating the region from the surrounding environment and ports for allowing the unit to be fluidly connected to the region.

According to the present invention, the bulkhead assembly includes a frame assembly with telescoping sections for allowing the frame assembly to be adjusted to fit within an opening of the region. In particular, the frame assembly is adjustable to fit within a variety of openings of different sizes while maintaining the region fluidly isolated from the surrounding environment. As shown in FIG. 4, opening 16 of enclosure 14 is illustrated as a doorway of a room. It is contemplated that opening 16 of enclosure 14 may be a window, a duct opening, or any other opening that allows access to region 12 of enclosure 14.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for decontaminating an enclosure defining a region, said system including:

- a decontamination unit for generating a vaporized sterilant, said decontamination unit comprising:
  - a housing defining a chamber therein, said housing having an inlet and an outlet fluidly communicating with said chamber;
  - a blower for conveying a carrier gas from said inlet, through said chamber and to said outlet of said housing; and
  - a generator for introducing a vaporized sterilant into said carrier gas conveyed through said housing; and
- a bulkhead assembly for connecting said decontamination unit to said enclosure, said bulkhead assembly comprising:
  - a barrier assembly for sealing an opening of said enclosure, said barrier assembly including:
    - a membrane resistant to said vaporized sterilant, said membrane traversing said opening of said enclosure; and
    - a first port and a second port for allowing said carrier gas to flow through the membrane;
  - an adjustable frame assembly for positioning said membrane of said barrier assembly in said opening of said enclosure, said adjustable frame assembly comprising:
    - an adjustable upper assembly for holding said membrane in sealing engagement with a top of said opening of said enclosure, said upper assembly having distal ends;

an adjustable lower assembly for holding said membrane in sealing engagement with a bottom of said opening of said enclosure, said lower assembly having distal ends; and a pair of adjustable side assemblies for holding said membrane in sealing engagement with opposite sides of said opening of said enclosure, each of said pair of side assemblies having distal ends, a notch formed in at least one of said distal ends of each of said pair of side assemblies, said notches defining a first pair of spaced-apart tabs disposed at one of said top of said opening or said bottom of said opening, said first pair of spaced-apart tabs dimensioned to receive one of said upper assembly or said lower assembly and to secure said upper assembly or said lower assembly in a press-fit fashion between said first pair of spaced-apart tabs, wherein said upper assembly or said lower assembly is inserted between said first pair of spaced-apart tabs from a front of said adjustable frame assembly, and wherein lengths of said upper assembly, said lower assembly and said pair of side assemblies are independently adjustable for independently varying a length of each side of said adjustable frame assembly;

an outlet conduit connected at one end to said outlet of said decontamination unit and at another end to said first port of said barrier assembly, said outlet conduit defining a flow path for conveying said carrier gas from said decontamination unit to said region of said enclosure; and a return conduit connected at one end to said inlet of said decontamination unit and at another end to said second port of said barrier assembly, said return conduit defining a flow path for conveying said carrier gas from said region to said decontamination unit.

2. The system as defined in claim 1, wherein said generator includes a nozzle for introducing a fine mist of aqueous sterilant into said carrier gas, wherein said aqueous sterilant vaporizes at an ambient air temperature of said region.

3. The system as defined in claim 1, further comprising a clamp assembly for attaching said outlet conduit to said outlet of said decontamination unit.

4. The system as defined in claim 1, further comprising a clamp assembly for attaching said return conduit to said inlet of said decontamination unit.

5. The system as defined in claim 1, wherein said vaporized sterilant is vaporized hydrogen peroxide.

6. The system as defined in claim 1, wherein said decontamination unit further comprises:
a removable diffuser disposed relative to said outlet of said housing for redirecting said carrier gas exiting said outlet of said chamber into a predetermined direction; and
a clamp assembly for positioning said removable diffuser relative to said outlet of said housing.

7. The system as defined in claim 1, wherein said decontamination unit further comprises:
a plurality of sensors for providing signals indicative of properties of said carrier gas in said region; and
a controller for controlling the operation of said decontamination unit, said controller connected to said plurality of sensors for determining a maximum rate that said vaporized sterilant may be injected into said carrier gas based on signals received from said plurality of sensors.

8. The system as defined in claim 7, wherein said plurality of sensors is disposed within said region.

9. The system as defined in claim 7, wherein said plurality of sensors is disposed within said chamber of said decontamination unit.

10. An apparatus as defined in claim 7, wherein said plurality of sensors includes at least one of the following: a humidity sensor, a temperature sensor and a vaporized hydrogen peroxide concentration sensor.

11. An apparatus for connecting a decontamination unit to an enclosure, said apparatus including:
an outlet conduit defining a flow path for conveying a carrier gas from said decontamination unit to said enclosure;
a return conduit defining a flow path for conveying said carrier gas from said enclosure to said decontamination unit;
a barrier assembly for sealing an opening of said enclosure, said barrier assembly including:
a membrane traversing said opening of said enclosure, said membrane resistant to a vaporized sterilant disposed in said enclosure; and
an inlet port and an outlet port for allowing said carrier gas to flow through the membrane; and
an adjustable frame assembly for securing said membrane of said barrier assembly into said opening of said enclosure, said adjustable frame assembly comprising:
an adjustable upper assembly for holding said membrane in sealing engagement with a top of said opening of said enclosure, said upper assembly having distal ends;
an adjustable lower assembly for holding said membrane in sealing engagement with a bottom of said opening of said enclosure, said lower assembly having distal ends; and
a pair of adjustable side assemblies for holding said membrane in sealing engagement with opposite sides of said opening of said enclosure, each of said pair of side assemblies having distal ends, a notch formed in at least one of said distal ends of each of said pair of side assemblies, said notches defining a first pair of spaced-apart tabs disposed at one of said top of said opening or said bottom of said opening, said first pair of spaced-apart tabs dimensioned to receive one of said upper assembly or said lower assembly and to secure said upper assembly or said lower assembly in a press-fit fashion between said first pair of spaced-apart tabs,
wherein said upper assembly or said lower assembly is inserted between said first pair of spaced-apart tabs from a front of said adjustable frame assembly, and
wherein lengths of said upper assembly, said lower assembly and said pair of side assemblies are independently adjustable for independently varying a length of each side of said adjustable frame assembly.

12. The apparatus as defined in claim 11, wherein said membrane is disposed between said adjustable frame assembly and said enclosure such that said adjustable frame assembly does not contact said vaporized sterilant in said enclosure.

13. The apparatus defined in claim 12, wherein said side assembly includes elongated telescoping sections dimensioned to extend the length of said side of said opening.

14. The apparatus defined in claim 12, wherein said upper assembly includes elongated telescoping sections dimensioned to extend the width of said top of said opening.

15. The apparatus defined in claim 12, wherein said lower assembly includes elongated telescoping sections dimensioned to extend the width of said bottom of said opening.

16. The apparatus defined in claim 12, further comprising:
at least one cross-brace assembly for holding said side assemblies against said sides of said opening.

17. The apparatus defined in claim 16, wherein one end of said cross-brace assembly is attached to one of said side assemblies and another end of said cross-brace is attached to another of said side assemblies.

18. The apparatus defined in claim 11, wherein said inlet port of said barrier assembly includes:
a first section disposed on one side of said membrane, a second section disposed on an opposite side of said membrane; and
a plurality of fasteners for securing said first section and said second section to said membrane.

19. The apparatus defined in claim 11, wherein said outlet port of said barrier assembly includes:
a first section disposed on one side of said membrane, a second section disposed on an opposite side of said membrane; and
a plurality of fasteners for securing said first section and said second section to said membrane.

20. The apparatus defined in claim 11, wherein said opening is a doorway.

21. A system as defined in claim 1, further comprising
a notch formed in the other of said distal ends of each of said pair of side assemblies, said notches defining a second pair of spaced-apart tabs disposed at the other of said top of said opening or said bottom of said opening, said second pair of spaced-apart tabs dimensioned to receive the other of said upper assembly or said lower assembly and to secure said upper assembly or said lower assembly in a press-fit fashion between said second pair of spaced-apart tabs, wherein said upper assembly or said lower assembly is inserted between said second pair of spaced-apart tabs from said front of said adjustable frame assembly.

22. An apparatus as defined in claim 11, further comprising:
a notch formed in the other of said distal ends of each of said pair of side assemblies, said notches defining a second pair of spaced-apart tabs disposed at the other of said top of said opening or said bottom of said opening, said second pair of spaced-apart tabs dimensioned to receive the other of said upper assembly or said lower assembly and to secure said upper assembly or said lower assembly in a press-fit fashion between said second pair of spaced-apart tabs, wherein said upper assembly or said lower assembly is inserted between said second pair of spaced-apart tabs from said front of said adjustable frame assembly.

\* \* \* \* \*